US012582389B2

(12) United States Patent
Pignata

(10) Patent No.: US 12,582,389 B2
(45) Date of Patent: Mar. 24, 2026

(54) URINE PRESERVATIVE COMPOSITION, DEVICE FOR SAMPLING URINE AND METHOD FOR MANUFACTURING A URINE SAMPLING DEVICE

(71) Applicant: VACUTEST KIMA S.R.L., Arzergrande (IT)

(72) Inventor: Sergio Pignata, Arzergrande (IT)

(73) Assignee: VACUTEST KIMA S.R.L., Arzergrande (IT)

( * ) Notice: Subject to any disclaimer, the term of this patent is extended or adjusted under 35 U.S.C. 154(b) by 616 days.

(21) Appl. No.: 18/043,127

(22) PCT Filed: Oct. 15, 2021

(86) PCT No.: PCT/IB2021/059506
§ 371 (c)(1),
(2) Date: Feb. 27, 2023

(87) PCT Pub. No.: WO2022/090850
PCT Pub. Date: May 5, 2022

(65) Prior Publication Data
US 2023/0309970 A1      Oct. 5, 2023

(30) Foreign Application Priority Data
Oct. 30, 2020    (IT) ........................ 102020000025885

(51) Int. Cl.
A61B 10/00          (2006.01)
(52) U.S. Cl.
CPC .................................. A61B 10/007 (2013.01)

(58) Field of Classification Search
CPC ........ A61B 10/007; A01N 1/00; A01N 31/02; A01N 37/06; A01N 37/36; A01N 59/14; A01P 1/00
See application file for complete search history.

(56) References Cited

U.S. PATENT DOCUMENTS

| | | | |
|---|---|---|---|
| 4,768,653 A | 9/1988 | Desai et al. |
| 6,261,844 B1 | 7/2001 | Smith et al. |
| 6,316,029 B1 | 11/2001 | Jain et al. |
| 2004/0013742 A1 | 1/2004 | Lin et al. |

FOREIGN PATENT DOCUMENTS

| | | |
|---|---|---|
| CN | 1179972 A | 4/1998 |
| CN | 1381273 A | 11/2002 |
| EP | 1581005 A1 | 9/2005 |

OTHER PUBLICATIONS

International Search Report for International Patent Application No. PCT/IB2021/059506, mailed Dec. 23, 2021.

(Continued)

*Primary Examiner* — Jennifer Wecker
*Assistant Examiner* — Steven Ray Castaneda
(74) *Attorney, Agent, or Firm* — Armstrong Teasdale LLP

(57) ABSTRACT

A urine preservative composition in solid form, based on boric acid and D-mannitol is disclosed. The urine preservative composition consists of boric acid from 37.0 to 69.7% by weight, D-Mannitol from 9.6 to 16.2% by weight, sodium bicarbonate and/or sodium carbonate from 18.0 to 25.0% by weight, polyvinylpyrrolidone from 0.1 to 2% by weight and sodium citrate and/or potassium sorbate from 0% to 24.2% by weight.

24 Claims, 5 Drawing Sheets

| Table n.8 | 0h | | 24h | | 48h | |
|---|---|---|---|---|---|---|
| | log10 UFC/ml | | log10 UFC/ml | | log10 UFC/ml | |
| | Vacutest Kima No additive Tube | Vacutest Kima Preservative Tube | Vacutest Kima No additive Tube | Vacutest Kima Preservative Tube | Vacutest Kima No additive Tube | Vacutest Kima Preservative Tube |
| E.coli | 2,92 | 2,96 | 3,86 | 2,50 | 3,88 | 2,13 |
| E.aerogenes | 3,24 | 3,23 | 3,49 | 3,15 | 3,61 | 2,81 |
| K. pneumoniae | 3,28 | 3,27 | 3,78 | 3,08 | 3,57 | 2,95 |
| P. aeruginosa | 3,35 | 3,37 | 3,29 | 3,18 | 3,00 | 2,64 |
| S. agalactiae | 3,11 | 3,15 | 3,06 | 2,86 | 3,01 | 2,34 |
| E. faecalis | 3,79 | 3,78 | 4,08 | 4,08 | 4,40 | 4,23 |
| S. saprophyticus | 3,16 | 3,06 | 2,53 | 2,82 | 2,45 | 2,58 |
| C. albicans | 3,66 | 3,65 | 3,72 | 3,53 | 3,50 | 3,49 |
| P. mirabilis | 3,47 | 3,51 | 3,92 | 2,60 | 3,94 | 2,20 |

(56) References Cited

OTHER PUBLICATIONS

Porter I.A. et al., Boric Acid Preservation of Urine Samples, British Medical Journal, May 10, 1969, pp. 353-355, vol. 2, BMJ Publishing Group Ltd., GB.

Nickander K.K. et al., Urine culture transport tubes: effect of sample volume on bacterial toxicity of the preservative, Journal of Clinical Microbiology, Apr. 1982, pp. 593-595, vol. 15, No. 4, ASM, US.

Meers P.D. et al., Bacteriostatic and bactericidal actions of boric acid against bacteria and fungi commonly found in urine, Journal of Clinical Pathology, Jun. 1, 1990, pp. 484-487, vol. 43, Issue 6, BMJ Publishing Group Ltd., GB.

Yilmaz, M.T., Minimum Inhibitory and Minimum Bactericidal Concentrations of Boron Compounds against Several Bacterial Strains, 2012, Turkish Journal of Medical Science, pp. 1423-1429, vol. 42, No. 8 Sup.2, Article 10,TÜBİTAK.

Lally R.T. et al., Evaluation of Mannitol Salt Agar with Oxacillin as a Screening Medium for Methicillin-Resistant *Staphylococcus aureus*, Journal of Clinical Microbiology, Oct. 1985, pp. 501-504, vol. 22, No. 4, American Society for Microbiology, US.

B. Raj Singh, Antibacterial Activity of Glycerol, Lactose, Maltose, Mannitol, Raffinose and Xylose Noto-are Medicine, Noto-are 17223318: Medicine, Jul. 19, 2014, pp. 1-3, © Noto-are.

| Table n.8 | 0h | | 24h | | | 48h | |
| --- | --- | --- | --- | --- | --- | --- | --- |
| | log10 UFC/ml | | log10 UFC/ml | | | log10 UFC/ml | |
| | Vacutest Kima No additive Tube | Vacutest Kima Preservative Tube | Vacutest Kima No additive Tube | Vacutest Kima Preservative Tube | | Vacutest Kima No additive Tube | Vacutest Kima Preservative Tube |
| E.coli | 2,92 | 2,96 | 3,86 | 2,50 | | 3,88 | 2,13 |
| E.aerogenes | 3,24 | 3,23 | 3,49 | 3,15 | | 3,61 | 2,81 |
| K. pneumoniae | 3,28 | 3,27 | 3,78 | 3,08 | | 3,57 | 2,95 |
| P. aeruginosa | 3,35 | 3,37 | 3,29 | 3,18 | | 3,00 | 2,64 |
| S. agalactiae | 3,11 | 3,15 | 3,06 | 2,86 | | 3,01 | 2,34 |
| E. faecalis | 3,79 | 3,78 | 4,08 | 4,08 | | 4,40 | 4,23 |
| S. saprophyticus | 3,16 | 3,06 | 2,53 | 2,82 | | 2,45 | 2,58 |
| C. albicans | 3,66 | 3,65 | 3,72 | 3,53 | | 3,50 | 3,49 |
| P. mirabilis | 3,47 | 3,51 | 3,92 | 2,60 | | 3,94 | 2,20 |

FIG.1

| Table n.9 | 0h log10 UFC/ml | | 24h log10 UFC/ml | | 48h log10 UFC/ml | |
|---|---|---|---|---|---|---|
| | Vacutest Kima No additive Tube | Vacutest Kima Preservative Tube | Vacutest Kima No additive Tube | Vacutest Kima Preservative Tube | Vacutest Kima No additive Tube | Vacutest Kima Preservative Tube |
| E.coli | 3,10 | 3,13 | 3,91 | 3,90 | 3,87 | 3,81 |
| E.aerogenes | 3,03 | 3,06 | 3,28 | 3,36 | 3,23 | 3,31 |
| K. pneumoniae | 3,47 | 3,48 | 3,29 | 3,00 | 3,21 | 2,38 |
| P. aeruginosa | 3,03 | 3,09 | 2,95 | 2,58 | 2,76 | 1,60 |
| S. agalactiae | 3,42 | 3,44 | 3,38 | 2,98 | 3,29 | 2,08 |
| E. faecalis | 3,01 | 3,02 | 3,27 | 3,25 | 3,48 | 3,27 |
| S. saprophyticus | 2,97 | 2,96 | 2,48 | 2,38 | 2,42 | 2,31 |
| C. albicans | 3,12 | 3,12 | 3,27 | 3,03 | 3,24 | 2,99 |
| P. mirabilis | 2,12 | 2,14 | 2,27 | 1,47 | 2,34 | 1,03 |

FIG.2

| Table n.10 | 0h | | 24h | | 48h | |
|---|---|---|---|---|---|---|
| | log10 UFC/ml | | log10 UFC/ml | | log10 UFC/ml | |
| | Vacutest Kima No additive Tube | Vacutest Kima Preservative Tube | Vacutest Kima No additive Tube | Vacutest Kima Preservative Tube | Vacutest Kima No additive Tube | Vacutest Kima Preservative Tube |
| E.coli | 3,33 | 3,31 | 3,90 | 2,30 | 3,91 | A.SV. |
| E.aerogenes | 3,11 | 3,11 | 3,37 | 2,68 | 3,44 | 1,90 |
| K. pneumoniae | 3,31 | 3,33 | 3,13 | 2,08 | 3,07 | A.SV. |
| P. aeruginosa | 3,71 | 3,71 | 3,58 | 3,45 | 3,33 | 2,38 |
| S. agalactiae | 3,16 | 3,16 | 3,13 | 2,79 | 3,05 | 2,34 |
| E. faecalis | 3,64 | 3,63 | 4,00 | 3,89 | 4,34 | 4,09 |
| S. saprophyticus | 3,42 | 3,40 | 3,06 | 3,14 | 3,03 | 3,11 |
| C. albicans | 3,21 | 3,23 | 3,17 | 3,16 | 3,09 | 3,11 |
| P. mirabilis | 2,96 | 2,98 | 3,27 | 2,87 | 3,32 | 2,76 |

FIG.3

| Table n.11 | 0h | | 24h | | 48h | |
| --- | --- | --- | --- | --- | --- | --- |
| | log10 UFC/ml | | log10 UFC/ml | | log10 UFC/ml | |
| | Vacutest Kima No additive Tube | Vacutest Kima Preservative Tube | Vacutest Kima No additive Tube | Vacutest Kima Preservative Tube | Vacutest Kima No additive Tube | Vacutest Kima Preservative Tube |
| E.coli | 3,11 | 3,06 | 3,93 | 3,94 | 3,93 | 3,91 |
| E.aerogenes | 3,25 | 3,21 | 3,70 | 3,60 | 3,85 | 3,69 |
| K. pneumoniae | 3,00 | 3,03 | 3,47 | 1,75 | 3,39 | A.SV. |
| P. aeruginosa | 2,99 | 3,02 | 2,89 | 3,08 | 2,72 | 2,51 |
| S. agalactiae | 3,53 | 3,53 | 3,42 | 3,03 | 3,40 | 2,86 |
| E. faecalis | 2,97 | 2,97 | 3,31 | 3,36 | 3,40 | 3,42 |
| S. saprophyticus | 3,11 | 3,13 | 2,51 | 2,99 | 2,42 | 2,68 |
| C. albicans | 3,42 | 3,39 | 3,59 | 3,25 | 3,41 | 3,25 |
| P. mirabilis | 3,14 | 3,11 | 3,64 | 2,95 | 3,71 | 2,89 |

FIG.4

| Table n.12 | 0h log10 UFC/ml | | 24h log10 UFC/ml | | 48h log10 UFC/ml | |
|---|---|---|---|---|---|---|
| | Vacutest Kima No additive Tube | Vacutest Kima Preservative Tube | Vacutest Kima No additive Tube | Vacutest Kima Preservative Tube | Vacutest Kima No additive Tube | Vacutest Kima Preservative Tube |
| E.coli | 3.07 | 3.07 | 3.92 | 3.92 | 3.90 | 3.90 |
| E.aerogenes | 3.15 | 3.13 | 3.60 | 3.41 | 3.74 | 3.54 |
| K. pneumoniae | 2.98 | 3.03 | 3.67 | 3.61 | 3.48 | 3.48 |
| P. aeruginosa | 3.09 | 3.02 | 3.05 | 2.83 | 2.78 | 2.43 |
| S. agalactiae | 2.98 | 3.00 | 2.87 | 2.94 | 2.86 | 2.99 |
| E. faecalis | 3.99 | 4.02 | 4.22 | 4.27 | 4.52 | 4.52 |
| S. saprophyticus | 3.09 | 2.97 | 2.41 | 2.74 | 2.48 | 2.54 |
| C. albicans | 3.25 | 3.23 | 3.31 | 3.10 | 3.09 | 3.07 |
| P. mirabilis | 2.96 | 3.12 | 3.49 | 2.97 | 3.55 | 2.77 |

FIG.5

URINE PRESERVATIVE COMPOSITION, DEVICE FOR SAMPLING URINE AND METHOD FOR MANUFACTURING A URINE SAMPLING DEVICE

CROSS-REFERENCE TO RELATED APPLICATION

This application is a National Stage Application of International Patent Application No. PCT/IB2021/059506, having an International Filing Date of Oct. 15, 2021, which claims priority to Italian Application No. 102020000025885, filed Oct. 30, 2020, the entire contents of which are hereby incorporated by reference herein.

FIELD OF APPLICATION

The present invention relates to a urine preservative composition, as well as to a device for sampling urine and to a method for manufacturing a urine sampling device.

PRIOR ART

As is known, the use of preservative additives allows the microbial load of a urine sample to be kept unaltered for 24-48 h, as an alternative to the more complex freezing of the sample itself. The use of preservative additives therefore allows samples to be collected without the need to be close to a laboratory, nor to have special equipment (cryogenic baths, thermal containers).

The use of additives in aqueous solution (described for example in patent application EP1581005A1 and in patent U.S. Pat. No. 4,768,653A) is limited, however, by the poor solubility in water of some components which may require the use of solvents other than water to improve the dissolution thereof (as described, for example, in U.S. Pat. No. 6,261,844).

Replacing glass urine collection tubes with PET tubes introduced an additional challenge. PET, unlike glass, allows the passage of water vapor. This phenomenon alters the correct additive/sample volume ratio, making the medical device (PET tube and preservative) unreliable.

Therefore, the need to guarantee the stability of the preservative over the lifetime of the PET tube (medical device) has caused the progressive abandonment of preservatives in solution in favor of preservatives in solid form.

The use of preservatives in solid form entails a number of problems.

A first problem is related to the fact that solid preservatives generally have a low dissolution rate in the urine sample. Therefore, the need arises to ensure a fast dissolution of the solid preservative in the samples.

A second problem is linked to the difficulties in dosing solid preservatives, generally in powder form. Therefore, the need arises to ensure a precise dosage of the preservative quantities in the test tubes in order to guarantee the correct concentration ratio between the preservative and the sample at the time of use.

These issues—although they have been addressed in different ways—are still current and deeply felt in the field.

To date, although various substances have been proposed on the market for the preservation of the microbial load in urine samples, such as Sodium Azide, Formaldehyde and Chlorhexidine, boric acid is the most widespread urine preservative due to its bacteriostatic capacity against *Pseudomonas* spp., as well as due to its low cost and ease of retrieval.

However, boric acid has a low solubility in water (46.5 g/l at 20° C.). Furthermore, if it is in crystalline form, it shows considerable difficulty in dissolving even under stirring. For this reason, boric acid is used in the form of an amorphous solid or finely divided powder in urine preservatives.

The bacteriostatic effect of boric acid is strictly dependent on its concentration. Furthermore, the difference between Minimum Inhibition Concentration (MIC) and Minimum Bactericidal Concentration (MBC) is very small. This also means that the variability of the sample volume sucked up with the vacuum tubes affects the effectiveness thereof, as reported by I. A. Porter, *Br Med J,* 1969, 2, pp. 353-355; K. K. Nickander et al, *J Clin Microb,* 1982, pp. 593-595; P. D. Meers, C. K. Chow, *J Clin Pathol,* 1990, 43, pp. 484-487; M. T. Yilmaz, *Turk J Med Sci,* 2012, 42, pp. 1423-1429.

It is known that the concentration of boric acid used in the tubes (1.5-2% W/V) with respect to the sample volume causes the death of the most sensitive Gram-negative bacterial strains (e.g.: *Klebsiella* sp.). The reduction in the amount of boric acid (0.8-0.6% W/V) improves the survival of the more sensitive strains, but leads to the loss of the inhibitory effect with respect to the more resistant Gram-positive strains (e.g.: *Clostridium perfringens*).

Boric acid is also known to significantly lower the pH of urine samples, reaching pH~5. The use of buffer substances therefore improves the bacteriostatic effect of boric acid with respect to some bacterial strains as described in patent U.S. Pat. No. 4,768,653. However, the boric acid concentration continues to be fatal for susceptible strains.

There remains therefore the need for a broad spectrum urine preservative which ensures a bacteriostatic effect both on vigorous strains and on delicate and difficult strains.

It is therefore necessary to compensate for the decrease in concentration of Boric acid with other substances that show bacteriostatic characteristics. Any co-formulants of boric acid must, however, be selected and calibrated in order to respect rapid dissolution times (about 5-10 minutes) and the absence of undissolved residues.

Furthermore, the preservative must be in solid form such as to be easily and precisely dosed in the test tubes.

Mercury-based solid preservative additives (e.g.: STABI-LUR®) used as an alternative have been abandoned due to the moratorium introduced by the European Community (EU Mercury Strategy, 2005). For these reasons, the products currently on the market continue to be based on boric acid.

A co-formulant of boric acid widely used in urine preservatives is mannitol, as described, for example, in patent U.S. Pat. No. 4,768,653.

In fact, mannitol forms stable and soluble complexes with Boric Acid and provides a good maintenance substrate for *Staphylococcus aureus* (R T Lally, M N Ederer, B F Woolfrey—Journal of Clinical Microbiology, 1985—Vol. 22, No. 4, pp. 501-504).

However, mannitol may also have a bactericidal effect if used in too high a concentration (B. Raj Singh, Noto-are Medicine, 2014, pp 1-3).

Another problem that arises with the use of mannitol is linked to the fact that mannitol is highly hygroscopic and its complexes tend to form sticky aggregates with medium-long dissolution times (20 minutes). This negatively affects the dissolution times of boric acid and mannitol-based urine preservatives.

As described in US2004/0137422A1, the use of freeze-drying in the preparation of urine preservatives in solid form allows having a rapidly dissolving and well-dosed product.

More in detail, the process provides that an appropriate formulation is poured into a test tube as an aqueous solution and then solidified at −50° C. The solvent water is eliminated by sublimation under high vacuum conditions (0.13-0.67 mbar) forming an amorphous and spongy solid.

The main problem of freeze-drying applied to urine preservatives is its high energy cost, as well as the long times required for vacuum evaporation.

The need to have a urine preservative composition in solid form which completely or at least partially overcomes the limits of the prior art described above is therefore very much felt.

In particular, the need is strongly felt to have a urine preservative composition in solid form which has adequate dissolution rates in urine samples without however having been subjected to freeze-drying.

Another strongly felt need is to have a urine preservative composition for urine in solid form which not only has adequate dissolution rates in urine samples without having been subjected to freeze-drying, but which is also easily dosable with volumetric/gravimetric systems.

A further strongly felt need is to have a urine preservative composition in solid form which not only has adequate dissolution rates in urine samples without having been subjected to freeze-drying, but which also offers a satisfactory bacteriostatic effect.

SUMMARY OF THE INVENTION

Therefore, the main object of the present invention is to eliminate, or at least reduce, the aforementioned problems relating to the prior art by providing a urine preservative composition in solid form which has adequate dissolution rates in urine samples without having been subjected to freeze-drying.

A further object of the present invention is to provide a urine preservative composition for urine in solid form which not only has adequate dissolution rates in urine samples without having been subjected to freeze-drying, but which is also easily dosable with volumetric/gravimetric systems.

A further object of the present invention is to provide a urine preservative composition in solid form which not only has adequate dissolution rates in urine samples without having been subjected to freeze-drying, but which also offers a satisfactory bacteriostatic effect.

DESCRIPTION OF THE DRAWINGS

The technical features of the invention are clearly identified in the content of the claims set out below and its advantages will become more readily apparent in the detailed description that follows, made with reference to the accompanying drawings, which represent one or more embodiments provided purely by way of non-limiting examples, in which:

FIG. 1 shows a table (Table 8) relating to the results of bacterial growth tests conducted on a urine preservative composition according to a first embodiment (formulation F01);

FIG. 2 shows a table (Table 9) relating to the results of bacterial growth tests conducted on a urine preservative composition according to a second embodiment (formulation F02);

FIG. 3 shows a table (Table 10) relating to the results of bacterial growth tests conducted on a urine preservative composition according to a third embodiment (formulation F03);

FIG. 4 shows a table (Table 11) relating to the results of bacterial growth tests conducted on a urine preservative composition according to a fourth embodiment (formulation F04); and FIG. 5 shows a table (Table 12) relating to the results of bacterial growth tests conducted on a urine preservative composition according to a fifth embodiment (formulation F05).

DETAILED DESCRIPTION

The present invention relates to a urine preservative composition.

Such preservative composition may be used in urine sampling devices.

Typically, a urine sampling device comprises: a test tube, preferably in PET, but possibly also in glass; and a cap for hermetically sealing the tube. Generally, the tube is vacuum-sealed. The urine preservative composition in solid form is dosed into the test tube before the tube is vacuum-sealed and then hermetically sealed with the cap.

The urine preservative composition according to the invention is in solid form and is based on boric acid and D-mannitol.

According to a general embodiment of the invention, the urine preservative composition consists of:

Boric acid from 37.0 to 69.7% by weight;

D-Mannitol from 9.6 to 16.2% by weight;

sodium bicarbonate and/or sodium carbonate from 18.0 to 25.0% by weight;

polyvinylpyrrolidone from 0.1 to 2% by weight; and sodium citrate and/or potassium sorbate, from 0% to 24.2% by weight.

It has surprisingly been found that by introducing Sodium Bicarbonate ($NaHCO3$) into a preservative composition for urine based on D-Mannitol and Boric Acid, the rate of solubilization of such preservative composition in a urine sample improves considerably, allowing a clear solution to be had in a much shorter time, with dissolution times in the order of 5-10 minutes, instead of 20 minutes. Such result is obtained without the preservative composition having been subjected to freeze-drying.

The sodium bicarbonate present in the preservative composition also has the secondary effect of acting as an anti-caking agent and mild dehydrating agent allowing to obtain a preservative composition in the form of a solid product which is grain-shaped and flowable.

As will be discussed later in the description, the degree of flowability of the composition also depends on the production method used.

The sodium bicarbonate present in the preservative composition also has a buffering effect on the acidity of the boric acid, stabilizing the pH of the sample.

Furthermore, once the preservative composition comes into contact with a urine sample inside a specially provided urine sampling device and begins to dissolve, the sodium bicarbonate present in the preservative composition decomposes, releasing carbon dioxide which saturates the inside of the tube (hermetically sealed) and stabilizes the sample, preventing the alteration thereof (modified atmosphere effect).

It has been verified that also sodium carbonate ($Na_2CO_3$) may be used to obtain the same advantages of increasing the solubilization rate, the stabilization and the anti-caking effect obtained with sodium bicarbonate ($NaHCO_3$).

Advantageously, sodium carbonate may therefore be present in the urine preservative composition in place of or in combination with sodium bicarbonate. Sodium bicarbonate is preferred as it is more readily available than sodium carbonate.

However, it has been noted that the introduction of Sodium Bicarbonate in a urine preservative composition based on D-Mannitol and Boric Acid has negative effects on the distribution of the urine sample mixed with the preservative on the surface of the culture media used for the determination of the microbial load present in the urine. The urine sample (with additive) distributed, according to the normal procedure, with an L-shaped microbiology spatula is in fact not very flowable and not homogeneous on the agar gel surface of the culture medium.

In general, to improve the ease of spreading and flowability of the urine sample (mixed with traditional preservatives based on boric acid and D-mannitol) on the surface of the culture medium it has been proposed (as described in U.S. Pat. No. 4,768,653) to use surfactants, usually polysorbates. The chemical nature and concentration of the surfactants must be carefully evaluated as they may be bactericidal due to their disintegrating effect on cell membranes.

It has surprisingly been found that by introducing Polyvinylpyrrolidone (PVP) in a mixture in a urine preservative composition based on D-Mannitol and Boric Acid and containing Sodium Bicarbonate, there is an effect comparable to that of surfactants, even though PVP is not a surfactant.

Polyvinylpyrrolidone (PVP) present in the preservative composition also has the secondary effect of facilitating the formation of very stable, but easily soluble solid aggregates.

By virtue of the presence of PVP, the urine preservative composition in solid form according to the invention not only has adequate dissolution rates in urine samples without having been subjected to freeze-drying, but also does not hinder the distribution of the urine sample mixed with the preservative on the surface of the culture media used for the determination of the microbial load present in the urine.

As will be discussed later in the description, it has been found that the bacteriostatic action of the urine preservative composition according to the invention varies according to the specific chemical composition. Advantageously, this may be exploited to define specific formulations of the aforesaid preservative composition in such a way that they exert differentiated bacteriostatic actions according to particular bacterial strains.

In the context of the general formulation of the preservative composition according to the invention, different formulations having different bacteriostatic actions have therefore been identified. In particular, the formulations differ from each other in the percentages by weight of sodium citrate and/or potassium sorbate. Neither sodium citrate and/or potassium sorbate are provided in one of the formulations.

According to a first embodiment of the invention, the urine preservative composition consists of:
  Boric acid from 62.5 to 69.7% by weight;
  D-Mannitol from 11.0 to 14.0% by weight;
  sodium bicarbonate from 19.0 to 23.0% by weight; and
  polyvinylpyrrolidone from 0.3 to 0.5% by weight.

Hereinafter, such first embodiment will be referred to as the first formulation or simply "F01."

Preferably, in such first formulation, the urine preservative composition consists specifically of:
  Boric acid 66.3% by weight;
  D-Mannitol 13.3% by weight;
  sodium bicarbonate 20.0% by weight; and
  polyvinylpyrrolidone 0.4% by weight.

According to a second embodiment, the urine preservative composition consists of:
  Boric acid from 55.0 to 65.0% by weight;
  D-Mannitol from 11.0 to 14.0% by weight;
  sodium bicarbonate from 18.0 to 22.0% by weight;
  polyvinylpyrrolidone from 1.0 to 2.0% by weight; and
  sodium citrate from 5.0 to 7.0% by weight.

Hereinafter, such second embodiment will be referred to as the second formulation or simply "F02."

Preferably, in such second formulation, the urine preservative composition consists specifically of:
  Boric acid 59.2% by weight;
  D-Mannitol 13.2% by weight;
  sodium bicarbonate 19.7% by weight;
  polyvinylpyrrolidone 1.3% by weight; and
  sodium citrate 6.6% by weight.

According to a third embodiment, the urine preservative composition consists of:
  Boric acid from 47.0 to 63.0% by weight;
  D-Mannitol from 10.0 to 15.0% by weight;
  sodium bicarbonate from 18.0 to 24.0% by weight;
  polyvinylpyrrolidone from 1.0 to 2.0% by weight; and
  sodium citrate from 8.0 to 12.0% by weight.

Hereinafter, such third embodiment will be referred to as the third formulation or simply "F03."

Preferably, in such third formulation, the urine preservative composition consists specifically of:
  Boric acid 55.9% by weight;
  D-Mannitol 13.2% by weight;
  sodium bicarbonate 19.7% by weight;
  polyvinylpyrrolidone 1.3% by weight; and
  sodium citrate 9.9% by weight.

According to a fourth embodiment, the urine preservative composition consists of:
  Boric acid from 37.0 to 57.0% by weight;
  D-Mannitol from 9.6 to 12.5% by weight;
  sodium carbonate from 19.0 to 25.0% by weight;
  polyvinylpyrrolidone from 0.1 to 0.8% by weight;
  sodium citrate from 4.2 to 8.2% by weight, and
  potassium sorbate from 10.0 to 16.0% by weight.

Hereinafter, such fourth embodiment will be referred to as the fourth formulation or simply "F04."

Preferably, in such fourth formulation, the urine preservative composition consists specifically of:
  Boric acid 44.4% by weight;
  D-Mannitol 11.0% by weight;
  sodium carbonate 22.2% by weight;
  polyvinylpyrrolidone 0.2% by weight;
  sodium citrate 7.4% by weight; and
  potassium sorbate 14.8% by weight.

According to a fifth embodiment, the urine preservative composition consists of:
  Boric acid from 40.0 to 55.0% by weight;
  D-Mannitol from 13.5 to 16.2% by weight;
  sodium bicarbonate from 19.5 to 25.0% by weight;
  polyvinylpyrrolidone from 0.1 to 0.8% by weight; and
  potassium sorbate from 12.0 to 18.0% by weight.

Hereinafter, such fifth embodiment will be referred to as the fifth formulation or simply "F05."

Preferably, in such fifth formulation, the urine preservative composition consists specifically of:
  Boric acid 48.0% by weight;
  D-Mannitol 14.8% by weight;
  sodium bicarbonate 22.2% by weight;
  polyvinylpyrrolidone 0.2% by weight;
  potassium sorbate 14.8% by weight.

In Table 1 below, all the five particular formulations listed above are reported:

TABLE 1

| Components | F-01 | F-02 | F-03 | F-04 | F-05 |
|---|---|---|---|---|---|
| D-Mannitol | 11-14% | 11-14% | 10-15% | 9.6-12.5% | 13.5-16.2% |
| Boric acid | 62.5-69.7% | 55-65% | 47-63% | 37-57% | 40-55% |
| Na Carbonate | — | — | — | 19-25% | — |
| Na Bicarbonate | 19-23% | 18-22% | 18-24% | — | 19.5-25% |
| K Sorbate | — | — | — | 10-16% | 12-18% |
| Na Citrate | — | 5-7% | 8-12% | 4.2-8.2% | — |
| PVP | 0.3-0.5% | 1-2% | 1-2% | 0.1-0.8% | 0.1-0.8% |

In Table 2 below, all the five preferred formulations listed above are reported:

TABLE 2

| Components | F-01 | F-02 | F-03 | F-04 | F-05 |
|---|---|---|---|---|---|
| D-Mannitol | 13.3% | 13.2% | 13.2% | 11.0% | 14.8% |
| Boric acid | 66.3% | 59.2% | 55.9% | 44.4% | 48.0% |
| Na Carbonate | — | — | — | 22.2% | — |
| Na Bicarbonate | 20% | 19.7% | 19.7% | — | 22.2% |
| K Sorbate | — | — | — | 14.8% | 14.8% |
| Na Citrate | — | 6.6% | 9.9% | 7.4% | — |
| PVP | 0.4% | 1.3% | 1.3% | 0.2% | 0.2% |

Solubility tests were conducted on all five of the above formulations F01, F02, F03, F04 and F05. In particular, the formulations reported in Table 2 were tested, by dosing 0.02 g per ml of sample of urine.

A dissolution time of less than 10 minutes was measured for all formulations. Complete dissolution was verified by checking under the microscope for the absence of undissolved crystals or deposits at the bottom of the tube. Table 3 below shows the dissolution times measured for each formulation.

TABLE 3

| Formulation | Dissolution time (minutes) |
|---|---|
| F-01 | 5 |
| F-02 | 7 |
| F-03 | 8 |
| F-04 | 8 |
| F-05 | 6 |

The solubility tests also showed that the particle size does not significantly affect the dissolution rate.

Preferably, the preservative composition for urine is in particle form (i.e. divided into solid particles) in order to increase the specific surface thereof and therefore the dissolution rate in the urine sample.

In particular, after mixing the components together, the urine preservative composition may be obtained in the form of solid particles with the following techniques:

by grinding the components;
by Spray Drying technique;
by mixing trough grinding part of the components in crystalline form with the amorphous powder obtained by Spray Drying of the remaining ones;
by wet granulation of the components.

More in detail, the grinding technique provides that the components of the preservative composition in the crystalline form available on the market are ground by means of a mill, which in particular may be a ball, cylinder or cone mill, provided with a calibrated mesh sieve to obtain a powder as homogeneous and uniform as possible.

As will be discussed hereafter, with the preservative compositions according to the invention the grinding leads to powders that are too thin and sensitive to electrostatic charges even with 2-3 mm sieves. This does not negatively affect the dissolution rate of the preservative composition, but its manipulability and dosability.

The Spray Drying technique consists in spraying a solution or a slurry of the components of the preservative composition in a flow of hot air which causes the drops to dry almost instantaneously, obtaining an amorphous solid. It has been found that the amorphous particle powder obtained with Spray Drying is difficult to handle as it is too thin and highly hygroscopic and therefore tends to stick to the walls of the distribution systems. This does not negatively affect the dissolution rate of the preservative composition, but its manipulability and dosability.

Mixed mixtures of solid particles obtained by grinding and by Spray Drying have the same limits set out above for ground particles and particles obtained by spray drying. The powder obtained is always too thin and hygroscopic, and therefore difficult to manipulate and dose.

The wet granulation technique consists in mixing the components of the preservative composition in a closed chamber with suitable mixing impellers where a liquid (preferably water) is nebulized which, together with the PVP present in the composition, allows an aggregate of spheroidal granules to be obtained. Subsequently these spheroidal granules are dried and, preferably, screened with calibrated mesh sieves to have a predefined particle size.

The urine preservative composition in the form of solid particles thus obtained turns out to be very flowable, not very dusty, stable, not very hygroscopic and only slightly sensitive to electrostatic charges. For these reasons, it is easy to dose in test tubes with automatic volumetric or gravimetric systems.

According to a totally preferred embodiment of the invention, the preservative composition for urine in particle form is not powdery, but is in the form of spheroidal granules. These granules may be aggregated or not aggregated with each other.

Preferably, the urine preservative composition in the form of spheroidal granules is obtained by a wet granulation process of the components, followed by drying of the granules thus obtained and optionally by sieving.

In particular, in producing the preservative composition using the wet granulation technique, a fast rotating body granulator (or High Shear Mixer Granulator) was used, provided with a nozzle which nebulizes type III water (ISO 3696:1987 standard) in an adequate quantity for obtaining the aggregates. The granulated mass thus obtained is mixed for a suitable time in order to guarantee the perfect formation of the granules, and is then discharged onto flat supports and dried in a ventilated chamber at 45° C. Subsequently, the dried mass is screened and any large aggregates shaped in grains with a conical mill with rotating blades provided with a 3 mm mesh sieve, to make the particle size of the product uniform.

Preferably, the aforesaid spheroidal granules have a particle size not exceeding 3 mm. The urine preservative composition in the form of spheroidal granules with a particle size not exceeding 3 mm has a flowability rate of between 5 and 11 g/s.

More preferably, the aforesaid spheroidal granules have a particle size comprised between 0.1 and 1 mm. The urine preservative composition in the form of spheroidal granules with a particle size between 0.1 and 1 mm has a flowability rate of between 5 and 8 g/s.

Even more preferably, the aforesaid spheroidal granules have a particle size comprised between 0.1 and 0.5 mm. The urine preservative composition in the form of spheroidal granules with a particle size between 0.1 and 0.5 mm has a flowability rate of between 5 and 7 g/s.

Most preferably, the aforesaid spheroidal granules have a particle size comprised between 0.3 and 0.5 mm. The urine preservative composition in the form of spheroidal granules with a particle size between 0.3 and 0.5 mm has a flowability rate of between 6 and 7 g/s.

The flowability rate was measured by applying the procedure provided by the European Pharmacopoeia 10th Ed., Chap. 2.9.16, 2.9.36 and 2.9.34 through funnel flowability tester with 10 mm hole.

Several flowability tests were carried out to evaluate the effect on the flowability rate of the chemical compositions in the different formulations and of the morphology of the solid particles (ground powder, granulated particles, and particle size).

In particular, the flowability tests were carried out using a Copley Flowability Tester BEP2 Funnel Attachment with a 10 mm hole as a flowability tester, provided with a digital scale and timer.

Table 4 below shows the results of the flowability tests carried out on different samples of preservative composition according to the invention all having the same formulation (F05), but with particles of different morphology.

In particular, the various types of powders may be obtained as illustrated below.

Ground powder: the solid components of the preservative composition, in the form in which they were found on the market, are weighed in a suitable container, coarsely mixed, poured into the hopper of a conical mill with a 5 mm sieve and ground a first time at low speed (~200 rpm) so as not to overheat the mixture. This preliminary ground powder is collected and reground, again with a conical mill on which the 3 mm screen has been mounted, at medium speed (~1500 rpm). The resulting powder is ready for testing.

Mixed SprayDry—Ground Powder: The components of the composition, except the sodium bicarbonate, are weighed for a total of 5 kg in a 20 L container. 10 liters of type III water (ISO 3696:1987 standard) are added and mixed at 200 rpm with a vertical butterfly mixer until a homogeneous and fluid mass is obtained. The Spray-Drying system is provided with a rotating atomizing nozzle pre-heated to 160° C. The previously prepared fluid mass is pumped with a peristaltic pump into the rotating nozzle which rotates at the speed of 35000 rpm. The fluid atomized inside the drying chamber by the rotation of the nozzle dries instantly and the dust is collected by a cyclone system. The bicarbonate, ground at 1000 rpm with a conical mill provided with a 1 mm sieve, is mixed roughly in the right proportion with the powder obtained from Spray-Drying and the whole is reground at 200 rpm with a conical mill provided with a 3 mm sieve. The resulting powder is ready for testing.

Particles obtained by granulation: the solid components of the composition, in the form in which they were found on the market, are weighed in a suitable container, mixed coarsely, poured into the mixing tank of a fast rotating body granulator (or High Shear Mixer Granulator). After closing the chamber door, the components are dry mixed for 5 minutes; then, without stopping the mixing, through a nozzle mounted on the lid of the tank, type III water (ISO 3696: 1987 standard) is atomized in a quantity of 1 per thousand divided over 10 minutes on the mass of the powdered components. The mass, which is aggregating under the action of the mixing blade, is mixed for another 5 minutes in order to guarantee the perfect formation of the granules and then discharged onto flat supports. Finally, it is dried in a ventilated chamber at 45° C. for 24 hours. Subsequently, the dried mass is screened with 0.5 mm and 1 mm sieves and any large aggregates shaped in grains at 100 rpm with a conical mill with rotating blades provided with a 3 mm mesh sieve to make the particle size of the product uniform. The resulting granulate is ready for the test.

The flowability is expressed as rate in grams/second (g/s). Each value is the average of 10 measurements. Increased rate indicates improved flowability.

TABLE 4

| Sample | Flowability speed (g/s) | Standard dev. | Note |
|---|---|---|---|
| Ground (0.5-0.1 mm) | 4.75 | 0.25 | Incomplete emptying of the container |
| Mix SprayDry/Ground (0.5-0.1) | — | — | No flowing |
| Ground (0.3-0.1 mm) | — | — | No flowing |
| Granulate (0.5-0.1 mm) | 6.72 | 0.37 | Complete emptying of the container |
| Granulate (2-1 mm) | 7.65 | 0.57 | Complete emptying of the container |
| Granulate (3-1 mm) | 10.85 | 0.17 | Complete emptying of the container |

The data reported in Table 4 show that the granulated urine preservative composition, i.e. in the form of spheroidal granules, is much more flowable than the same composition in the form of powders obtained by grinding.

The granulated urine preservative composition in addition to being more flowable is also not very dusty, stable, not very hygroscopic and only slightly sensitive to electrostatic charges. For these reasons, it is easier to dose in test tubes with automatic volumetric or gravimetric systems.

The data reported in Table 4 also show that the larger the diameter of the granules, the higher the flowability rate.

To avoid distribution and dosing problems, however, it is preferable that the flowability rate does not exceed 8 g/s, and even more preferably that it remains between 6 g/s and 7 g/s.

Flowability tests were carried out on the five different formulations of the urine preservative composition according to the invention, adopting the same morphology and particle size.

Table 5 below shows the flowability results detected on samples of the five formulations F01, F02, F03, F04 and F05, having solid particles consisting of spheroidal granules with particle size of between 0.5 and 1 mm.

TABLE 5

| Sample (spheroidal granules 0.5-1 mm) | Flowability rate (g/sec) | St. dev. | Note |
|---|---|---|---|
| Mixture F01 | 5.72 | 0.45 | Complete emptying of the container |
| Mixture F02 | 6.25 | 0.27 | Complete emptying of |

TABLE 5-continued

| Sample (spheroidal granules 0.5-1 mm) | Flowability rate (g/sec) | St. dev. | Note |
|---|---|---|---|
| | | | the container |
| Mixture F03 | 7.15 | 0.36 | Complete emptying of the container |
| Mixture F04 | 7.32 | 0.23 | Complete emptying of the container |
| Mixture F05 | 6.92 | 0.38 | Complete emptying of the container |

The data reported in Table 5 show that the different formulations have substantially comparable flowability, with a difference for the formulation F01 which is a little less flowable and with more flowing differences, as evidenced by a higher standard deviation value.

As has already been pointed out above, the bacteriostatic action of the urine preservative composition according to the invention varies according to the specific chemical composition. Advantageously, this may be exploited to define specific formulations of the aforesaid preservative composition in such a way that they exert differentiated bacteriostatic actions according to particular bacterial strains.

The different formulations F01, F02, F03, F04 and F05 were tested to evaluate the functionality thereof in terms of bacteriostatic action on different bacterial strains.

More in detail, the functionality of the various formulations was tested using bacterial strains in suspension at suitable concentrations expressed in UFC (Colony Forming Units) in a sterile urine pool, to mimic the bacterial load present in urine samples. The bacterial strains used are shown in Table 6 below.

TABLE 6

| Organism | ATCC* |
|---|---|
| Escherichia coli | 25922 |
| Enterobacter aerogenes | 13048 |
| Klebsiella pneumoniae | 13883 |
| Pseudomonas aeruginosa | 27853 |
| Streptococcus agalactiae | 13813 |
| Enterococcus faecalis | 29212 |
| Staphylococcus saprophyticus | 15305 |
| Candida albicans | 10231 |
| Proteus mirabilis | 29245 |

*American Type Culture Collection.

Starting from a suspension in Tryptone Soy Broth, by means of appropriate dilutions, for each bacterial strain, in a sterile pool 2 suspensions were prepared with bacterial load equal to about 1000 CFU/ml for the first and 100 CFU/ml for the second, hereinafter referred to as Stock Suspensions.

Each of these Stock Suspensions was used to fill two series of Vacutest Kima tubes, one of which containing the preservative composition, named in the tables of the accompanying figures as "Preservative Tube," and the other without any additives, named in the tables of the accompanying figures as "No Additive Tube."

Within one hour of transferring the bacterial suspension to the tubes, an aliquot was taken from each tube of each series which was seeded in duplicate on Petri dish media described in Table 7 below according to the modified Miles-Misra method; these plates were incubated aerobically at 35(±1)° C. for 24 hours and subsequently stored at 6(±2)° C. These seedings are identified as "0h" in the accompanying figures.

TABLE 7

| Organism | Culture medium used |
|---|---|
| Escherichia coli | Tryptone soy agar |
| Enterobacter aerogenes | Tryptone soy agar |
| Klebsiella pneumoniae | Tryptone soy agar |
| Pseudomonas aeruginosa | Tryptone soy agar |
| Streptococcus agalactiae | Tryptone soy agar +5%s. mutton |
| Enterococcus faecalis | Tryptone soy agar |
| Staphylococcus saprophyticus | Tryptone soy agar |
| Candida albicans | Tryptone soy agar |
| Proteus mirabilis | C.L.E.D. agar |

After seeding, the "No additive Tubes" were then stored at 6(±2)° C.; the "Preservative Tubes" were instead stored at 24 (±1) ° C.

After a storage time of 24 hours and 48 hours from each tube of each series an aliquot was taken which was seeded in duplicate and incubated as described in the previous point. These seedings are identified as "24 h" and 48 h" in the tables of the accompanying figures.

At the end of the incubation period the plates with the "24 h" seedings were stored in the fridge, while at the end of the incubation period of the plates with the "48 h" seedings all the plates were counted (0h, 24 h, 48 h), recording the average value obtained from the count of each pair of plates. The values obtained are expressed as log 10 of the CFU/ml.

The results of these tests are reported in Tables 8 to 12, shown respectively in the accompanying FIG. 1 to 5. The acronym More in detail, Table 8 (FIG. 1) shows the results of the tests conducted on a urine preservative composition according to the formulation F01. Table 8 shows that the formulation F01 is aggressive for Coli and sensitive strains (Klebsiella, Enterobacter, Coli, Streptococcus, Proteus) which show stunted growth at both 24 h and 48 h. Advantageously, the composition with formulation F01 may therefore be used in the case in which it is desired to specifically detect more resistant bacterial strains, such as Enterococcus Faecalis, Staphylococcus Saprophyticus and Candida Albicans.

More in detail, Table 9 (FIG. 2) shows the results of the tests conducted on a urine preservative composition according to the formulation F02. Table 9 shows that the formulation F02 allows good growth for E. Coli, but is too aggressive for Klebsiella, Pseudomonas, Streptococcus, Proteus which show stunted growth at both 24 h and 48 h. Advantageously, the preservative composition with the formulation F02 may therefore be used in the case in which it is desired to specifically detect bacterial strains, such as Escherichia Coli and Enterobacter Aerogenes.

More in detail, Table 10 (FIG. 3) shows the results of the tests conducted on a urine preservative composition according to the formulation F03. Table 10 shows that the formulation F03 allows a good growth not only for the more resistant strains (Enterobacter and Pseudomonas), but also for Proteus, but it is too aggressive for Klebsiella and Coli enough to lead to no growth in 48 h. Advantageously, the preservative composition with the formulation F03 may therefore be used in the case in which it is desired to specifically detect bacterial strains, such as Enterobacter Faecalis, Pseudomonas Aeruginosa, Candida Albicans and Staphylococcus Saprophyticus.

More in detail, Table 11 (FIG. 4) shows the results of the tests conducted on a urine preservative composition according to the formulation F04. Table 11 shows that the formulation F04 allows a good preservation for almost all bacterial strains. For *Staphylococcus*, stunted growth is observed; for *Klebsiella* the formulation F04 is too aggressive enough to lead to no growth after 48 h. Advantageously, the preservative composition with the formulation F04 may therefore be used in the case in which it is desired to selectively inhibit bacterial strains, such as *Klebsiella Pneumoniae* and *Streptococcus Agalactiae*.

Table 12 (FIG. 5) shows the results of the tests conducted on a urine preservative composition according to the formulation F05. Table 12 shows that the formulation F05 allows good growth for all bacterial strains. Advantageously, the preservative composition with formulation F05 offers a satisfactory broad-spectrum bacteriostatic effect and may therefore be used to detect all bacterial strains.

The urine preservative composition according to the invention according to the formulation F05 not only has adequate dissolution rates in urine samples without having been subjected to freeze-drying and is easily dosable with volumetric/gravimetric systems, but also has a satisfactory broad-spectrum bacteriostatic effect.

The present invention also relates to a device for sampling urine.

Such urine sampling device includes:
  a test tube, preferably made in PET;
  a cap for hermetically sealing the test tube; and
  a dosed quantity of urine preservative composition in solid form.

The aforementioned urine preservative composition for urine in solid form is a preservative composition according to the invention, and in particular as described above.

Preferably, the aforesaid dosed quantity of preservative composition for urine in solid form is comprised between 0.022 and 0.018 g/ml of urine sample, said test tube having a predefined nominal volume of urine containment. Preferably, said nominal volume is comprised between 2 ml and 11 ml.

The present invention also relates to a method of manufacturing a urine sampling device.

This production method comprises the following operating steps:
  (a) providing a test tube, preferably made in PET, with a predefined nominal urine containment volume;
  (b) placing a quantity of urine preservative composition in a solid form in said tube, dosed according to said predefined nominal volume;
  (c) creating a predefined vacuum in the test tube; and
  (d) hermetically sealing said test tube with a cap, maintaining said predefined vacuum.

The aforementioned urine preservative composition for urine in solid form is a preservative composition according to the invention, and in particular as described above.

Preferably, the urine preservative composition according to the invention is to be stored in a protected environment to avoid the risk that it may absorb humidity from the environment.

Preferably, step b) of placing inside the test tube a quantity of preservative composition for urine in solid form is carried out in such a way as to reduce the time of exposure to ambient air, so as to reduce the risk of absorption of environmental humidity. In particular, such step b) may be carried out in a controlled atmosphere.

The invention allows numerous advantages to be obtained which have been explained in the course of the description.

The urine preservative composition in solid form according to the invention has adequate dissolution rates in urine samples without having been subjected to freeze-drying.

The urine preservative composition in solid form according to some embodiments of the invention not only has adequate dissolution rates in urine samples without having been subjected to freeze-drying, but is also easily dosable with volumetric/gravimetric systems.

The urine preservative composition in solid form according to some embodiments of the invention not only has adequate dissolution rates in urine samples without having been subjected to freeze-drying, but also offers a satisfactory bacteriostatic effect.

The urine preservative composition in solid form according to some preferred embodiments of the invention not only has adequate dissolution rates in urine samples without having been subjected to freeze-drying, but is also easily dosable with volumetric/gravimetric systems and at the same time offers a satisfactory bacteriostatic effect.

The invention thus conceived therefore achieves its intended purposes.

Of course, in its practical implementation it may also assume different forms and configurations from the one illustrated above, without thereby departing from the present scope of protection.

Furthermore, all details may be replaced with technically equivalent elements and dimensions, shapes and materials used may be any according to the needs.

What is claimed is:

1. A urine preservative composition in solid form, based on boric acid and D-mannitol, wherein the urine preservative composition consists of:
  boric acid from 37.0 to 69.7% by weight;
  D-Mannitol from 9.6 to 16.2% by weight;
  sodium bicarbonate and/or sodium carbonate from 18.0 to 25.0% by weight;
  polyvinylpyrrolidone from 0.1 to 2% by weight; and
  sodium citrate and/or potassium sorbate, from 0% to 24.2% by weight.

2. The urine preservative composition of claim 1, in particle form, preferably in the form of spheroidal granules, aggregated or non-aggregated with each other.

3. The urine preservative composition of claim 2, wherein said spheroidal granules have a grain size not exceeding 3 mm.

4. The urine preservative composition of claim 3, wherein the urine preservative composition has a flowability rate between 5 and 11 g/s, measured according to European Pharmacopoeia 10^Ed. chap. 2.9.16, 2.9.36 and 2.9.34 using a funnel-shaped flowability tester with 10 mm hole.

5. The urine preservative composition of claim 2, wherein said spheroidal granules have a grain size between 0.1 and 1 mm.

6. The urine preservative composition of claim 5, wherein the urine preservative composition has a flowability rate between 5 and 8 g/s, measured according to European Pharmacopoeia 10^Ed. chap. 2.9.16, 2.9.36 and 2.9.34 using a funnel-shaped flowability tester with 10 mm hole.

7. The urine preservative composition of claim 2, wherein said spheroidal granules have a grain size between 0.1 and 0.5 mm.

8. The urine preservative composition of claim 7, wherein the urine preservative composition has a flowability rate between 5 and 7 g/s, measured according to European Pharmacopoeia 10^Ed. chap. 2.9.16, 2.9.36 and 2.9.34 using a funnel-shaped flowability tester with 10 mm hole.

9. The urine preservative composition of claim 2, wherein said spheroidal granules have a grain size between 0.3 and 0.5 mm.

10. The urine preservative composition of claim 9, wherein the urine preservative composition has a flowability rate between 6 and 7 g/s, measured according to European Pharmacopoeia 10˚Ed. chap. 2.9.16, 2.9.36 and 2.9.34 using a funnel-shaped flowability tester with 10 mm hole.

11. The urine preservative composition of claim 1, obtained by a wet granulation process of the components, followed by drying of the granules thus obtained and optionally by sieving.

12. The urine preservative composition of claim 1, consisting of:
> boric acid from 62.5 to 69.7% by weight;
> D-Mannitol from 11.0 to 14.0% by weight;
> sodium bicarbonate from 19.0 to 23.0% by weight; and
> polyvinylpyrrolidone from 0.3 to 0.5% by weight.

13. The urine preservative composition of claim 12, consisting of:
> boric acid 66.3% by weight;
> D-Mannitol 13.3% by weight;
> sodium bicarbonate 20.0% by weight; and
> polyvinylpyrrolidone 0.4% by weight.

14. The urine preservative composition of claim 1, consisting of:
> boric acid from 55.0 to 65.0% by weight;
> D-Mannitol from 11.0 to 14.0% by weight;
> sodium bicarbonate from 18.0 to 22.0% by weight;
> polyvinylpyrrolidone from 1.0 to 2.0% by weight; and
> sodium citrate from 5.0 to 7.0% by weight.

15. The urine preservative composition of claim 14, consisting of:
> boric acid 59.2% by weight;
> D-Mannitol 13.2% by weight;
> sodium bicarbonate 19.7% by weight;
> polyvinylpyrrolidone 1.3% by weight; and
> sodium citrate 6.6% by weight.

16. The urine preservative composition of claim 1, consisting of:
> boric acid from 47.0 to 63.0% by weight;
> D-Mannitol from 10.0 to 15.0% by weight;
> sodium bicarbonate from 18.0 to 24.0% by weight;
> polyvinylpyrrolidone from 1.0 to 2.0% by weight; and
> sodium citrate from 8.0 to 12.0% by weight.

17. The urine preservative composition of claim 16, consisting of:
> boric acid 55.9% by weight;
> D-Mannitol 13.2% by weight;
> sodium bicarbonate 19.7% by weight;
> polyvinylpyrrolidone 1.3% by weight; and
> sodium citrate 9.9% by weight.

18. The urine preservative composition of claim 1, consisting of:
> boric acid from 37.0 to 57.0% by weight;
> D-Mannitol from 9.6 to 12.5% by weight;
> sodium carbonate from 19.0 to 25.0% by weight;
> polyvinylpyrrolidone from 0.1 to 0.8% by weight;
> sodium citrate from 4.2 to 8.2% by weight, and
> potassium sorbate from 10.0 to 16.0% by weight.

19. The urine preservative composition of claim 18, consisting of:
> boric acid 44.4% by weight;
> D-Mannitol 11.0% by weight;
> sodium carbonate 22.2% by weight;
> polyvinylpyrrolidone 0.2% by weight;
> sodium citrate 7.4% by weight; and
> potassium sorbate 14.8% by weight.

20. The urine preservative composition of claim 1, consisting of:
> boric acid from 40.0 to 55.0% by weight;
> D-Mannitol from 13.5 to 16.2% by weight;
> sodium bicarbonate from 19.5 to 25.0% by weight;
> polyvinylpyrrolidone from 0.1 to 0.8% by weight; and
> potassium sorbate from 12.0 to 18.0% by weight.

21. The urine preservative composition of claim 20, consisting of:
> boric acid 48.0% by weight;
> D-Mannitol 14.8% by weight;
> sodium bicarbonate 22.2% by weight;
> polyvinylpyrrolidone 0.2% by weight; and
> potassium sorbate 14.8% by weight.

22. A urine sampling device, comprising:
> a test tube, preferably made of PET;
> a cap for hermetically sealing the test tube; and
> a dosed quantity of a urine preservative composition in solid form,
> wherein said urine preservative composition in solid form is the urine preservative composition of claim 1.

23. The urine sampling device of claim 22, wherein said dosed quantity of urine preservative composition in solid form is between 0.022 and 0.018 g/ml of urine sample, said test tube having a predefined nominal urine containment volume between 2 ml and 11 ml.

24. A method for manufacturing a urine sampling device, comprising:
> (a) providing a test tube, preferably made of PET, with a predefined nominal urine containment volume;
> (b) placing a quantity of urine preservative composition in solid form in said test tube, dosed according to said predefined nominal urine containment volume;
> (c) creating a predefined vacuum in the test tube; and
> (d) hermetically sealing said test tube with a cap, maintaining said predefined vacuum,
> wherein said urine preservative composition in solid form is the urine preservative composition of claim 1.

\*   \*   \*   \*   \*